United States Patent [19]

Curtis et al.

[11] Patent Number: 5,310,563
[45] Date of Patent: May 10, 1994

[54] DENTAL MATERIAL AND METHOD FOR APPLYING PREVENTATIVE AND THERAPEUTIC AGENTS

[75] Inventors: John Curtis, Bloomsbury; Salim Nahoo, Piscataway; Michael Prencipe, East Windsor, all of N.J.

[73] Assignee: Colgate-Palmolive Company, New York, N.Y.

[21] Appl. No.: 782,700

[22] Filed: Oct. 25, 1991

[51] Int. Cl.$^5$ .................. A61K 6/00; A61K 6/08; A61K 33/40; A61K 31/74

[52] U.S. Cl. .................. 424/616; 106/35; 424/53; 424/613; 424/614; 424/615; 433/203.1; 433/215; 433/226; 433/228.1

[58] Field of Search .......... 106/35; 424/63, 613–616; 433/215, 226, 228.1, 203.1

[56] References Cited

U.S. PATENT DOCUMENTS

| | | | |
|---|---|---|---|
| 2,541,851 | 2/1951 | Wright | 260/37 |
| 3,060,935 | 10/1962 | Riddell | 128/260 |
| 3,138,820 | 6/1964 | Sterling | 15/506 |
| 3,339,547 | 9/1967 | Drabkowski | 128/260 |
| 3,379,193 | 4/1968 | Monaghan | 128/136 |
| 3,416,527 | 12/1968 | Hoef | 128/260 |
| 3,527,219 | 9/1970 | Greenberg | 128/260 |
| 3,624,909 | 12/1971 | Greening | 32/40 |
| 3,688,406 | 9/1972 | Porter et al. | 32/40 |
| 3,844,286 | 10/1974 | Cowen | 128/260 |
| 3,855,171 | 12/1974 | Wegehaupt et al. | 260/37 SB |
| 3,862,919 | 1/1975 | Nitzsche et al. | 260/18 S |
| 3,913,229 | 10/1975 | Driskell et al. | 32/15 |
| 3,964,164 | 6/1976 | Hesselgren | 32/1 |
| 4,064,628 | 12/1977 | Weitzman | 32/14 |
| 4,173,219 | 11/1979 | Lentine | 128/260 |
| 4,371,493 | 2/1983 | Minuto | 264/236 |
| 4,428,373 | 1/1984 | Seid et al. | 604/77 |
| 4,531,914 | 7/1985 | Spinello | 433/136 |
| 4,554,154 | 11/1985 | White | 424/16 |
| 4,650,665 | 3/1987 | Kronenthal et al. | 424/435 |
| 4,931,096 | 6/1990 | Fujisawa et al. | 106/35 |
| 4,944,947 | 7/1990 | Newman | 424/435 |
| 5,051,130 | 9/1991 | Futami et al. | 106/35 |

OTHER PUBLICATIONS

Dow Corning 3179 Dilatant Compound, Dow Corning Corporation, 1987.

Primary Examiner—Shep K. Rose
Attorney, Agent, or Firm—Michael J. McGreal; Robert C. Sullivan

[57] ABSTRACT

A dental composition is produced from a dilatant silicone polymer composition by dispersing a bioactive component in the polymer composition. The dental composition is shaped and pressed against the teeth and gum surfaces and allowed to remain in place for a period of time sufficient to release the active component to the tooth and gums. The dilatant rheological properties enable the dental composition to be pushed under the gingival flap to remove food particles and treat tooth and gum surfaces below the gum line. The composition is sufficiently plastic to be easily removed from the teeth without pieces breaking and adhering to tooth surfaces.

10 Claims, 2 Drawing Sheets

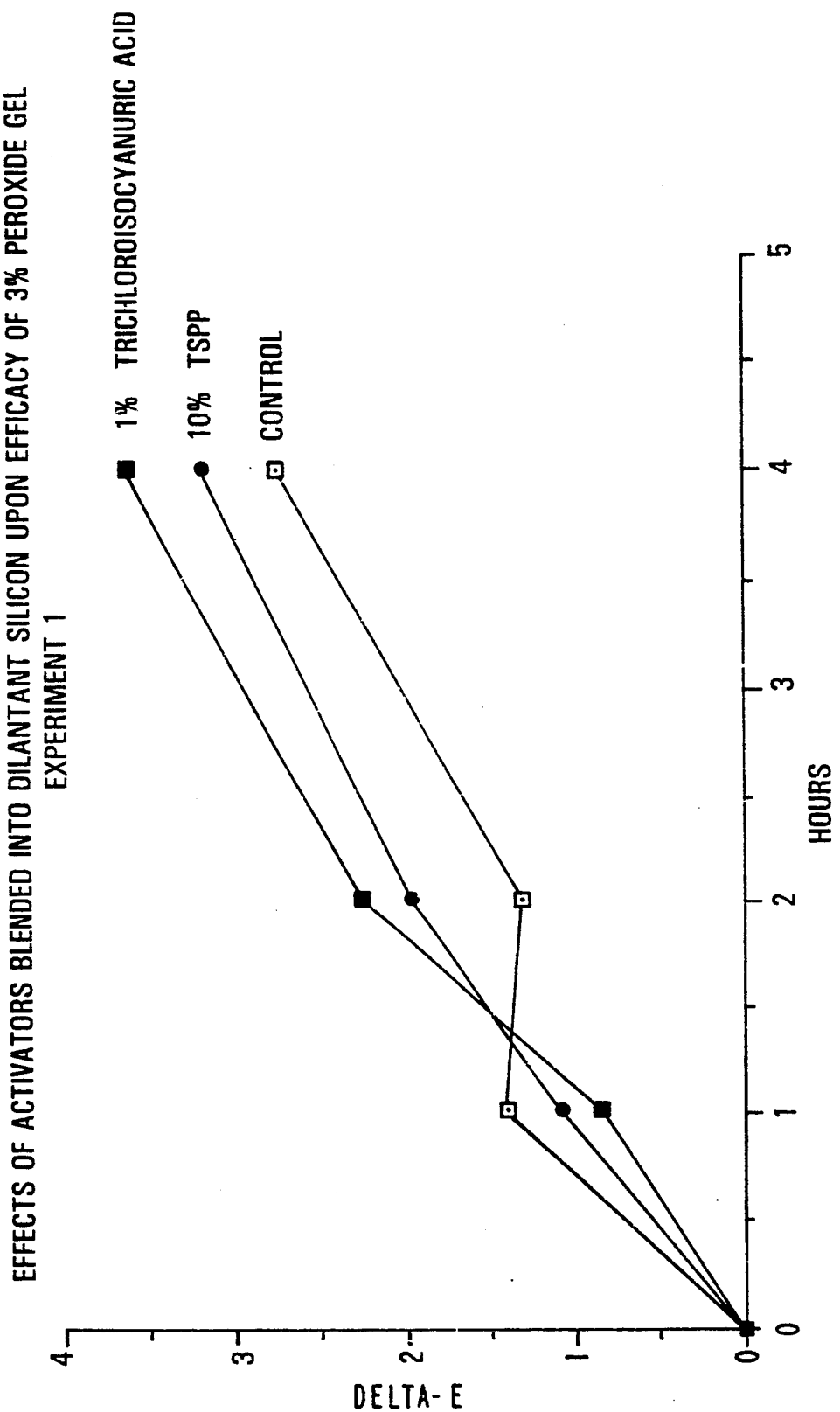

DENTAL MATERIAL AND METHOD FOR APPLYING PREVENTATIVE AND THERAPEUTIC AGENTS

FIELD OF THE INVENTION

The present invention is directed to a dental material to apply a dentifrice or active agent to the tooth and gum surfaces. More specifically, the invention relates to an elastic putty-like material that is readily moldable to the tooth and gum surface and which encapsulates medicaments and dentifrices.

BACKGROUND OF THE INVENTION

In the field of dental hygiene numerous devices and products have been developed to reduce and prevent gum disease and tooth decay. Gum disease typically results in the inflammation of the gum tissue by the accumulation of bacterial plaque on tooth surfaces and in particular on the tooth surface below the gum line. The plaque as well as the acids that decay teeth are produced by the sugars present in the mouth. Dental diseases can be often prevented with the use of mechanical, dietary, chemical and immunological plaque control. The toothbrush and dental floss in cooperation with a dentifrice are the usual convenient dental hygiene devices to control tooth decay and gum disease. These devices do have their limitations in effectively cleaning and treating some areas of the teeth. Other devices which have been produced include products that include a dentifrice or antibacterial product incorporated within the product. These products may be in the form of a chewable component, paste or a liquid such as a mouthwash.

One example of this type of product is disclosed in U.S. Pat. No. 4,554,154. This product includes a substrate of a malleable plastic or aluminum strip having a biologically acceptable adhesive on the outer surface of the strip. The malleable plastic is disclosed as a strip that covers and adapts to the shape of the tooth surfaces. The strip may be a chewable plastic strip, plastic foam shape, chewing stick, capsule or cloth, an encapsulated cleaning stick, toothbrush bristle containing many fine parallel fibers so that the bristle ends conform to the shape of the tooth surface, or a fiber chewing gum. The substrate may carry a biologically acceptable adhesive by impregnation, lamination, coating or encapsulation. The adhesive is disclosed as containing a remineralizing agent, immunological agent, enzyme, lysozyme or antibacterial agent. The plastic strip is intended to be chewed in a manner similar to chewing gum to treat the chewing surfaces of the teeth. This device does not effectively enter the spaces between the teeth or under the gum tissue to remove food particles and apply the dentifrice to the tooth surface.

U.S. Pat. No. 4,531,914 relates to a dental device for gingival retraction and gum conditioning prior to a subsequent dental procedure such as crowning. The dental device is disclosed as a moldable, flowable, coherent plastic material. In one embodiment, the disclosed material is a plastic thixotropic medium such as a hydrolyzed high polymer silicone that is rendered hydrosorbent by incorporating fibers into plastic. The balance and placement of the fibers and plastic are reported to be critical because the essential physical property of the medium is antithetical to the other and an imbalance renders the device ineffective. In use, the mass of thixotropic material is provided with a layer of the fibers to render the surface of the mass hydrosorbent. The fibers may be impregnated with a vascoconstricting agent to arrest bleeding of traumatized gingival tissue. The material is pressed into place to push gingival flap away from the tooth surface and remove any fluids from the area to enable the dental procedure to proceed. This device does not apply dentifrices to the tooth surface and does not remove plaque and debris from between the teeth.

U.S. Pat. No. 3,138,820 relates to a tooth cleaning and gum massaging device in the form of a strip or pellet of a sponge-like material that expands in the presence of moisture. The material is disclosed as a cellular body having a dentifrice, germicide, or medicament. The device is chewed to massage the gums and to release the dentifrice through the pores of the sponge-like material.

U.S. Pat. No. 3,964,164 relates to a material for applying preventive and therapeutic agents to the teeth of a patient. The material is disclosed as a moldable mass as a carrier which may contain an active agent. The moldable carrier may be a plastic or elastic impression mass such as impression wax or wax compositions, hydrocolloidal impression masses and rubber impression masses. The molding material may further be a gelatin or agar having a calcium sulfate reactor. In the disclosed embodiments the molding material is initially plastic to be applied to the teeth and conform to the tooth surface. The molding material is then allowed to set or polymerize into a tough or viscous material. This product has the disadvantage of requiring the user to mix or heat the components of the molding material to activate the setting action of the material. The material must further be molded quickly when activated to prevent the material from hardening before being shaped.

U.S. Pat. No. 4,650,665 relates to an absorbable biologically compatible putty-like composition used as a matrix from which immunologically or pharmacologically active agents can be introduced into the body to provide sustained release of the agent. The disclosed matrix is a mixture of calcium stearate, dextran and castor oil. Dextran is disclosed as the most preferred absorption enhancing agent.

U.S. Pat. No. 3,598,123 relates to a bandage for administering drugs by absorption. The device includes a backing member including a pressure-sensitive adhesive. A systemically active drug is encapsulated in microcapsules which are distributed throughout the adhesive. The encapsulating material is disclosed as polyvinyl alcohol, polyvinylacetate, collagen, wax, silicon rubbers and others.

Other types of dental treating devices include those which have a shaped member to conform to the teeth of the user. These devices often have a foam or sponge-like material that can be formed and shaped around the teeth to deliver a dentifrice or other material. Some of these devices include a substantially horse shoe-shaped tray to apply a dentifrice to the teeth. Examples of these devices may be found in U.S. Pat. Nos. 3,339,547, 3,844,286, 3,527,219, 3,416,527, 3,688,406 and 3,379,193.

The above-noted devices and compositions do not provide a convenient and effective means for removing food particles from between the teeth and for applying a dentifrice or medicament to the tooth surface below the gum line. Many of these devices cannot be easily molded and cannot be comfortably worn by the user. Some of the molding compositions which have been previously used require heat or chemical activation which increases the burden of using the composition. The present invention is directed to a composition that is easily molded to conform to the contours of the teeth and gums to apply a dentifrice to the tooth surface under the gum line.

SUMMARY OF THE INVENTION

The present invention is directed to a dilatant polymeric plastic composition that can be easily molded and shaped to conform to the tooth surface of the user. The plastic composition is preferably sufficiently flexible to be easily pressed against the teeth and gently lift the gum tissue away from the tooth to expose the gingival surface. The plastic composition preferably contains at least one dentifrice and/or a medicament which can be transferred to the tooth and gum surface to effectively apply a coating of the medicament. In one alternative embodiment a dentifrice and/or medicament can be applied to the plastic composition as a coating after it has been previously formed into a shape corresponding to the tooth surface. The plastic composition is applied to the tooth and gum surface by pressing against the teeth gently with the fingers to form it to the shape of the teeth or gums. The polymeric composition is sufficiently pliable to be pressed under the gingival flap without irritation or trauma to the gum tissue. The composition is allowed to remain in contact with the tooth surface for a sufficient period of time to medicate the gum tissue and treat the teeth.

The polymeric plastic composition is preferably a disposable elastic polymeric composition having nontoxic dilatant properties such that the composition can be molded easily and remain in place when pressed against the tooth surface. The plastic composition should further resist breaking into small pieces when removed and provide easy molding and deformation at room temperature without becoming too soft at body temperature. The composition should have sufficient rebound and resistance to slump to remain in place and to retain its shape when molded. The composition should further be stable for extended periods of time and effectively encapsulate a dentifrice or other active component without interaction or decomposition of the active component. In a preferred embodiment of the invention the composition is a dilatant silicone polymer. The preferred silicone polymer compositions are substantially non-erodible, non-irritating and non-absorbable by the tissues in the mouth.

The composition in the preferred from of the invention contains at least one dentifrice or medicament dispersed and encapsulated in the polymeric plastic composition. The dentifrice may be, for example, a fluoride composition. The medicament may be a germicidal composition such as hexachlorophene or chlorohexidine or an anti-bacterial composition such a triclosan. The composition may alternatively include an antibiotic, hemostatic agent, antifungal agent, tooth whitener, remineralizing agent, enzyme, flavorant or odor absorbing agent.

In an alternative preferred embodiment, the dental composition contains at least one dispersed active agent such as a hypochlorite-providing compound or a pyrophosphate. A second active component is applied to the composition immediately before use to prevent interaction of the two components during storage. The dental composition may be pressed against the tooth and gum surface to mold the material. The molded dental material is then removed and a coating of the second active component is applied to the impression. The coated impression is reinserted to the tooth surface to deliver the active component.

BRIEF DESCRIPTION OF THE DRAWINGS

The following is a brief description of the drawings in which:

FIG. 3 is a graph illustrating the effects of activators in the dental composition upon efficacy of topically applied peroxide bleaching agents.

DETAILED DESCRIPTION OF THE INVENTION

Figure 1:
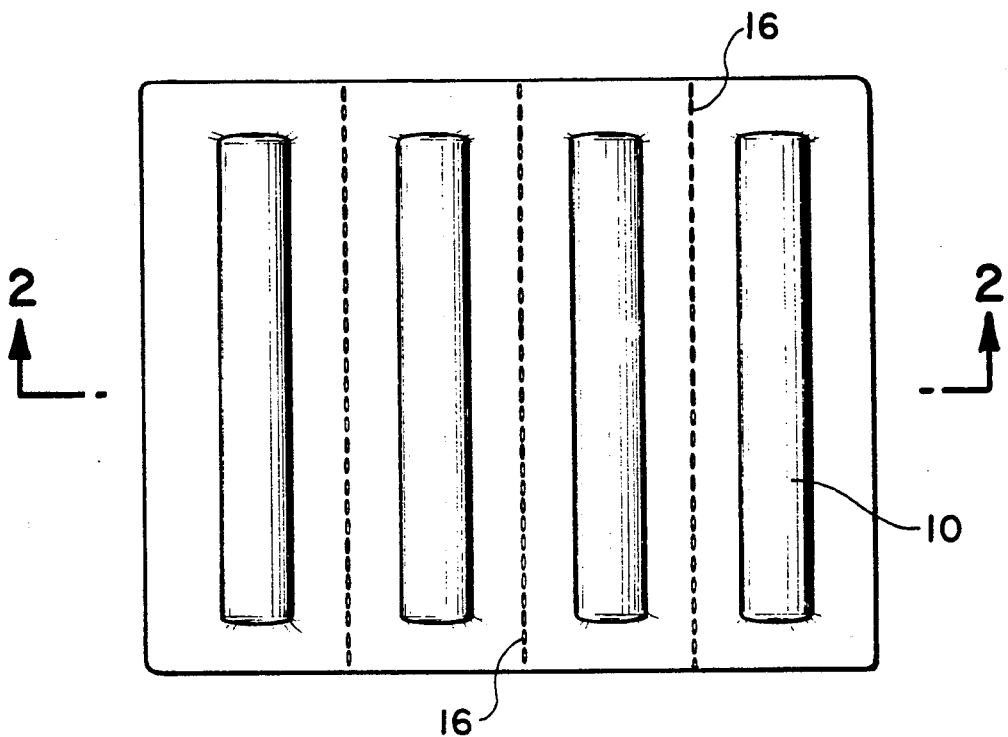
FIG. 1 is to plan view of the dental composition in a preferred embodiment of the invention.

The disadvantages and limitations of the prior dental treating devices are obviated by the present invention while providing convenient and effective treatment of the teeth and gum surfaces and particularly to the teeth surfaces below the gum line. The present invention provides a polymeric plastic composition containing a dentifrice, activator or medicament encapsulated therein which can be readily delivered to the user.

The polymeric plastic composition preferably is a nontoxic and nonirritating elastic composition having good dilatant rheological characteristics. The composition should further have good resistance to slump or flow and good stability over a range of temperatures for an extended period of time. The plastic composition is preferably substantially non-tacky to avoid excessive sticking to the teeth and gums and is non-bioerodable and non-bioabsorbable. Preferably the composition is sufficiently pliable to be easily molded and shaped to be applied to the teeth and to be forced under the gum line without irritation or trauma to the gum tissue.

In a preferred embodiment of the invention, the plastic composition is a plastic thixotropic medium such as a hydrolyzed high molecular weight silicone polymer composition. One example of a silicone polymer composition suitable for use in the present invention is disclosed in U.S. Pat. No. 2,541,851. The silicone polymers are typically polysiloxanes having a high viscosity and are sufficiently flexible to be molded and shaped while being sufficiently coherent to be handled as a mass. These plastic materials are non-absorbent and impervious to moisture. In a preferred embodiment, the dilatant silicone is a polysiloxane polymer composition sold under the tradename Dow Corning 3179 Dilatant Compound by Dow Corning Corporation. This product is a coral-colored silicone polymer having a high elasticity, and high bounce while offering ease of movement under low mechanical force. The polymer has a plasticity of about 65-100 mils as determined by ASTM D 926, a specific gravity of about 1.10–1.18 as determined by ASTM D 972, a slump of about 0.75 (maximum) and a rebound of about 70%.

One example of a suitable composition as described in U.S. Pat. No. 2,541,851 is produced from a polydimethyl silicone oil that is heated with a boron compound such as pyroboric acid or ethyl borate to form a quasi-rubbery gel. A fine particle size filler, such as silica or titanium dioxide, is mixed with the gel to produce the putty-like composition.

The Dow Corning 3179 Dilatant Compound is a mixture of polydimethylsiloxane, dimethyl cyclosiloxanes and hydroxy-terminated polydimethylsiloxane polymers. The inert additives include titanium dioxide, silica, quartz, boric acid, thixotrol (TM) and glycerine. Alternative plastic compounds which may be suitable in practicing the invention, include for example, hydrocolloids and some unpolymerized butadiene rubbers.

The plastic composition for use in the invention in one embodiment is prepared by mixing a pharmacological or therapeutically active or bioactive component with the dilatant polymeric compound. In a preferred embodiment the active component is mechanically mixed or kneaded with the plastic composition to uniformly mix and disperse the active component. The active component may be a liquid or solid which is compatible with the plastic composition. Solid active components are generally preferred having a particle size of about 5 to about 400 microns and most preferably a particle size of about 100 to 200 microns. The small particle size is generally preferred to increase the available surface area of the active component to provide efficient treatment of the teeth and gums. The smaller particle sizes further reduce the grittiness of the dental composition. Liquid active components and solutions of the active component can also be used and dispersed in the plastic dental composition. The active component in an alternative embodiment may be first encapsulated in a water soluble or water permeable matrix such as for example a glass matrix of a high molecular weight carbohydrate or microcapsules as well known in the art. The encapsulated active component may then be dispersed in the plastic matrix.

The plastic composition preferably includes at least one active component in the form of a dentifrice, pharmacological or other therapeutic or bioactive component. The dentifrice is preferably a fluoride or fluoride-containing compound such as sodium fluoride, potassium fluoride, ammonium fluoride, sodium difluoride, potassium difluoride, ammonium difluoride, sodium silicofluoride, zinc fluoride, stannous fluoride. Other dentifrices include, for example, unreases, acid phosphates, calcium carbonate, and magnesium carbonate. Examples of acid phosphates which may be used include, for example, orthophosphoric acid, monosodium phosphate, monopotassium phosphate, disodium phosphate, dipotassium phosphate, monoammonium phosphate, hemisodium phosphate and sodium hexametaphosphate salts. The dentifrice is preferably included in the polymeric plastic composition in an amount sufficient to provide a topical concentration of about 5 to about 1000 ppm at the tooth surface. It has been found that effective fluoride treatment can be obtained by including the fluoride compound in the plastic composition in the amount of about 5% to 20% and preferably 10% to 15% by weight of the polymeric plastic composition to provide the delivery of a therapeutically affective amount of the active component.

Other active components which may be incorporated within the plastic composition include hydrogen peroxide or peroxide producing components such as PVP $H_2O_2$ or Carbamide $H_2O_2$ Fluoride, tooth acidulating agents such as buffered or acidulated phosphofluoride, sodium monofluorophosphate, plaque control agents, tartar control agents such as tetrasodium pyrophosphate, antibiotics to treat pyorrhea and gingivitis, teeth whitening and bleaching agents such as trichloroisocyanuric acid, pH buffering or adjusting agents, antifungal agents, remineralizing agents, hemostatic agents, immunological agents and nonionic and cationic antibacterials such as benzothonium chloride, acetyl trimethyl ammonium bromide, sanguinaria, triclosan (nonionic), tetracycline, cetyl pyridinium chloride, and benzothonium chloride. The polymeric plastic matrix may further include an odor absorbing or absorbing component such as activated charcoal, activated silica, activated alumina or zeolite. Additional active components include vitamins, such Vitamin A, surfactants and flavors including anise, peppermint, wintergreen, spearmint, fruit flavors and the like. Among the pharmacologically active agents which may be included are, for example anti-cancer agents, stimulants, bone growth agents, antigens, hormones, steroids, anti-inflammatory agents and analgesic agents.

In one embodiment of the invention the dental composition includes a uniform blend of a fluoride compound, a remineralizing agent and an antibacterial agent. The composition in the preferred form of the invention is formed by rolling or other means into a cylindrical shape and pressing against the teeth and gums of the area to be treated and between adjacent teeth. The dental composition may be pressed into place using the fingers or by other suitable mechanical pressure. The dilatant rheological properties of the dental composition gently lift the gingival flap away from the tooth surface when moderate pressure is applied. The dental composition is pressed between the gingival flap and the tooth and over the outer surface of the gingival flap. The dental compound may be pressed and molded around the tooth and gum surfaces to substantially conform it to the natural contour of the teeth and gums. In this manner the dental compound can be applied without discomfort to the user or substantial irritation or trauma to the gums. The user is able to talk or sleep without discomfort and without the dental composition dislodging from the tooth and gum surface.

The dental compound is applied directly to the tooth and gum surface such that the active components are transferred from the composition to the teeth and gums. The dental composition may be applied for a few minutes to several hours depending on the desired treatment. Generally, the dental composition is applied for about 15 minutes. The dilatant rheological properties of the composition are such that the composition adheres sufficiently to the tooth surface to remain in place while permitting easy removal without pieces sticking to the teeth. The composition preferably has sufficient adhesive characteristics to remove food particles and plaque from between the teeth and surfaces below the gum line. The dental composition may be easily removed from the tooth surface by peeling gently. Although the dental composition may be reapplied to a different location after treatment, generally the composition is disposed after the initial use.

The dental compound may also be formed to the shape of the teeth or gum surface by pressing against the teeth and gums, removed, coated on the surface bearing the impression of the teeth or gums with an active agent, and then put back into contact with the teeth or gums. In this way an active ingredient can be delivered in a larger dose, or in the alternative, a second active ingredient applied to the teeth and gums. In addition, the dental composition need not contain any active ingredients with the active ingredients added to the surface after it has been formed to the shape of the teeth and gums. However it is preferred that the dental composition incorporate at least one active ingredient.

In an alternative preferred embodiment, the dental composition may be used to apply two components that are generally incompatible or reactive with each other. The dental composition will generally contain at least one active component dispersed therein. The composition is molded to the tooth surface thereby forming a dental impression. The molded compound is removed from the tooth surface and a second active component is applied to the impression. The composition is again pressed against the tooth and gum surface to apply the active components. This method enables the user to apply an effective amount of the active component directly under the gum line and between the teeth. Alternatively the dental composition may be shaped by hand and the second active component applied to the dental composition rather than forming an impression by pressing against the teeth.

The second component applied to the molded dental composition is generally in the form of a paste, powder or liquid. The application of the second component to the molded composition has the advantage of allowing a high concentration of the active component to be applied to the tooth and gum surface. The active component applied to the molded composition may be an unstable component such as a peroxide which would not endure prolonged storage when encapsulated or dispersed in the polymeric composition. The active component applied as a coating to the molded compound is further advantageous where the active components are reactive or otherwise incompatible. The active component dispersed in the dental composition may be an activator or component producing a synergstic effect with the component applied to the molded composition.

In one embodiment of the invention the dental composition is used to apply a bleaching agent to the teeth. A bleaching activator is dispersed within the dental composition. Suitable activators include, for example, trichloroisocyanuric acid and tetrasodium pyrosphate. The dental composition is pressed against the teeth to form a dental impression. A hydrogen peroxide-providing compound is applied to the impression which is then pressed against the tooth surface. It has been found that trichloroisocyanuric acid reacts with hydrogen peroxide to produce a biologically active species of oxygen referred to as singlet oxygen, which has been found to be an efficient bleaching and whitening agent. The combination of hydrogen peroxide and trichloroisocyanuric acid tends to raise the pH of the system thereby producing perhydroxy radicals which are also effective bleaching agents. Hydrogen peroxide is, however, unstable at high pH and, therefore, it is desirable to apply the hydrogen peroxide-providing compound immediately before use to maximize the tooth whitening effect of the singlet oxygen and the perhydroxy radical.

Pre-encapsulating the active component is particularly advantageous where the component is volatile, unstable or incompatible with a second component is the polymeric plastic composition. Active components which may be pre-encapsulated include, for example, flavors such as vanilla, or unstable vitamins or pharmacological compounds. In one embodiment of the invention the active component may be encapsulated by mixing with a high molecular weight carbohydrate or disaccharide and extruding above the glass transition temperature of the encapsulating component to form a glassy matrix. The matrix is generally extruded into rods which can be ground to the desired particle size. In the preferred embodiment the encapsulated active component is reduced to a particle size of about 5 microns to 400 microns. Preferably the encapsulating medium is a water soluble or water permeable component to allow the release of the encapsulated component.

Other encapsulating materials which may be employed include the organopolysiloxane polymers that a heat curable or room temperature vulcanizable. Another suitable encapsulating material include the hydrophilic polymers of monoesters of an olefinic acid, such as acrylic acid and methacrylic acid. When these polymers are used, the active component is usually dissolved in a solvent to enhance the passage of the drug through the polymer. Additional encapsulating materials include polyvinylalcohol, polyvinylacetate, plasticized polyvinylchloride, nylon, collagen, gelatin, polyethylene wax and hydrogenated castor oil.

Any number of encapsulation process can be used to prepare the encapsulated active component. The active component may be dispersed in a solvent and mixed with the encapsulation material. Alternatively, a solution of the active component can be used to impregnate the solid encapsulating material. The solid encapsulating material may then be reduced to fine microcapsules by grinding. Other methods of producing the encapsulated active component result in a thin shelled capsule having a hollow center filled with the active component. The method employed in producing the encapsulated active component is not critical to the invention and may be any of the usual methods as well known in the art.

In a further alternative embodiment of the invention the active component may be absorbed or adsorbed onto a carrier such as for example cellulose fibers or an inorganic particulate. The carrier with the absorbed or adsorbed active component may then be dispersed in the plastic composition.

Figure 2:
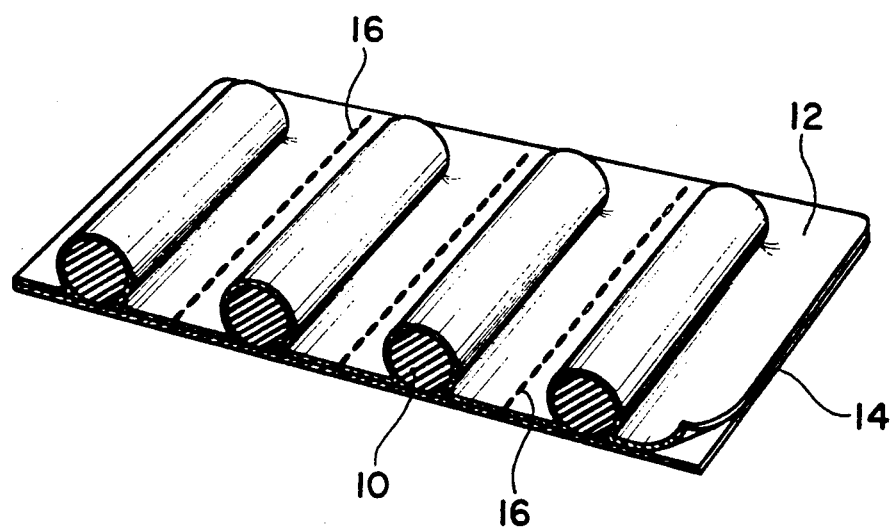
FIG. 2 is a cross sectional view of the dental composition of the invention taken along line 2—2 of FIG. 1.

In one embodiment of the invention as illustrated in FIG. 1, the dental composition is prepared and packaged in a plurality of discrete strips 10. The strips 10 of the dental composition are wrapped in a plastic wrapping film. The composition contains at least one active component dispersed in the polymeric composition and contain a coating of a second active component. The packaged dental composition may further include a coating of a second active component such the second active component can be applied by simply pressing the dental composition over the area to be treated. In the preferred embodiment of FIG. 2 two sheets of the wrapping film 12,14 are laminated around the dental composition and heat sealed between the individual pieces. Perforations or other frangible lines 16 are provided between the pieces. Preferably the wrapping film is heat sealable to provide a peelable seal enveloping the individual pieces. In use the wrapping films are separated by peeling back a corner of package to obtain a single piece of the dental composition without unwrapping the remaining pieces.

EXAMPLE I

A dental composition may be prepared from a silicone copolymer sold under the tradename Dow Corning 3179 Dilatant Compound by Dow Corning Corporation. The silicone compound has plasticity of 65–100 mils as determined by ASTM D 926, a specific gravity of 1.14 at 25° C. and a slump of about 0.5 inches. The composition is a blend of dimethylsiloxane, dimethylcyclosiloxanes and hydroxy-terminated polydimethylsiloxanes. To 100 grams of the silicone copolymer is blended 5.0 grams of stannous fluoride and 5.0 grams of chlorohexidine. The composition is blended to uniformly mix the components. The dental composition is rolled by hand into cylindrical shaped pieces and pressed with the fingers against the tooth surface and gum tissue. The dental composition is allowed to remain in place for a period of time and then removed by gently pulling from the teeth.

EXAMPLE II

A dental composition was prepared from the silicone polymer as in Example I. The silicone copolymer was blended with about 1.5% by weight $H_2O_2$ in the form of $PVP/H_2O_2$ to uniformly disperse the active component. The prepared composition was applied to extracted human molars for a period of about 24 hours at 37° C. At the end of 24 hours the dental composition was removed and the teeth examined using a Gardiner Colorimeter. The results of the analysis are presented in Table 1.

For comparative purposes, a 10% solution of urea peroxide and a commercial tooth powder containing 1.5% by weight $H_2O_2$ as $PVP/H_2O_2$ were applied to extracted molars for 24 hours at 37° C. The teeth were then removed from the compositions and examined using a Gardiner Colorimeter. The results are shown in Table 1 below.

TABLE 1

| Bleaching Agent | pH | White L | Yellow b | Whitening Increase $\sqrt{(L^2 + b^2)}$ |
|---|---|---|---|---|
| 10% Urea Perox Solution | 5 | 3.7 | −5.0 | 6.2 |
| Silicone Compound 1.5% $PVP/H_2O_2$ | — | 8.7 | −3.5 | 9.3 |
| Tooth Powder 1.5% $PVP/H_2O_2$ | — | 10.2 | −3.3 | 10.7 |

The Gardiner Colorimeter represents the color of the tooth surface in terms of tristimulus values for red, blue and green spectral colors measured as L, (a) and (b). The value of L corresponds to the lightness and corresponds closely to visual estimates of this quantity. A positive value for (b) indicates yellowness and minus value for blueness. The positive value for (a) indicates redness and minus value indicates greenness. In the measurements of the teeth the value of (a) is essentially zero and may be disregarded in calculating color difference $\sqrt{(L)^2+(a)^2+(b)^2}$.

The above data demonstrate the silicone compound is effective in delivering active components to the tooth surface. The differences of the white and yellow measurements between the silicone compound and the tooth powder are considered to be negligible.

EXAMPLE III

This example demonstrates the effect of a hydrogen peroxide activator in the dental composition. The dental composition was a dilatant silicone composition as in Example I. Two test samples of the dental composition were prepared containing 1% by weight trichloroisocyanuric acid and 10% tetrasodium pyrophosphate. A control sample of the dental composition was prepared containing no added activator.

Caries free, naturally stained extracted human molars were pumiced with Mynol TM tooth cleaning paste and the color of each tooth was determined using a Minolta ChromaMeter. The teeth were impressioned in the dental composition containing 1% trichloroisocyanuric acid, 10% tetrasodium pyrophosphate and the control composition. To the resulting impressions, 5 grams of Pluronic TM gel containing 3% hydrogen peroxide was added and the teeth were wetted and inserted into the impression. For each tooth five readings of L, a and b were taken at zero hours (control) 1 hour, 2 hours, and 4 hours. The change in color was then calculated using the equation.

$$\Delta E=[(\Delta L)^2+(\Delta a)^2+(\Delta b)^2]^{\frac{1}{2}}$$

The color values were plotted against the treatment time as shown in FIG. 3. The delta E values correspond to the lightness of the teeth with the values increasing with lightness. The data demonstrate that the activator dispersed in the dental composition is released to increase the bleaching efficiency of the hydrogen peroxide. The greatest whitening effect resulted from the sample containing 1.0% trichlorocyanuric acid.

The above examples are considered to be exemplary of the preferred embodiment and are not intended to be limiting. It will be readily understood by those skilled in the art that numerous alternative embodiments can be produced without departing from the scope of the invention.

What is claimed is:

1. A method of whitening teeth comprising:
   shaping a dental composition to conform to a tooth surface, said dental composition comprising a non-absorbing, non-erodible dilatant silicone polymer composition and at least one bioactive whitening agent;
   contacting said dental composition against said tooth surface for sufficient time to release said whitening agent and whiten said teeth; and
   removing said dental composition from said tooth surface.

2. The method of claim 1, wherein said whitening agent is a hydrogen peroxide providing compound.

3. The method of claim 2, wherein said whitening agent is selected from the group consisting of $PVP/H_2O_2$, carbamide $H_2O_2$ and mixtures thereof.

4. A method of whitening teeth, said method comprising
   pressing a dental composition against a tooth and gum surface to mold said composition to form a dental impression, said dental composition comprising a non-erodible, non-absorbing, moldable, dilatant polymeric silicone compound and an activator for activating a tooth whitening agent;
   removing the molded dental composition from said tooth surface substantially without deforming the molded composition;
   applying a tooth whitening compound to said molded dental composition, said tooth whitening compound being activated by said activator; and
   reapplying the dental composition to the tooth surface for sufficient time to enable said tooth whitening compound and said activator to react and to deliver said tooth whitening compound to said tooth surface.

5. The method of claim 4, wherein the tooth whitening agent is selected from the group consisting of $PVP/H_2O$, carbamide $H_2O_2$ and mixtures thereof.

6. The method of claim 5, wherein said activator is selected from the group consisting of tetrasodium pyrophosphate and trichloroisocyanuric acid.

7. A shaped, disposable dental composition for delivering a bioactive compound and treating tooth surfaces and gum tissue, said dental composition comprising a substantially non-absorbing, non-erodible dilatant plastic silicone polymer composition and a first bioactive compound uniformly dispersed in said dilatant plastic polymeric composition;

a coating on said polymer composition of a second bioactive compound;

wherein said dental composition is moldable to conform and adhere to tooth and gum surfaces whereby said first and second bioactive compounds are delivered to tooth and gum surfaces.

8. The composition of claim 7, wherein said composition is a tooth whitening composition and wherein said first bioactive compound is an activator for a hydrogen peroxide providing compound and said second bioactive compound is a hydrogen peroxide providing compound.

9. The composition of claim 8, wherein said activator is selected from the group consisting of tetrasodium pyrophosphate and trichloroisocyanuric acid and said hydrogen peroxide providing compound is selected from the group consisting of $PVP/H_2O_2$ and carbamide $H_2O_2$.

10. The composition of claim 7, wherein said composition is a tooth whitening composition, said first bioactive compound being a hydrogen peroxide providing tooth whitening compound and said second bioactive compound being an activator compound for said whitening compound.

* * * * *